(12) United States Patent
Kim

(10) Patent No.: US 10,801,010 B2
(45) Date of Patent: Oct. 13, 2020

(54) COMPOSITION FOR INDUCING DIRECT TRANSDIFFERENTIATION INTO OLIGODENDROCYTE PROGENITOR CELLS FROM SOMATIC CELLS AND USE THEREOF

(71) Applicant: UNIST(ULSAN NATIONAL INSTITUTE OF SCIENCE AND TECHNOLOGY), Ulsan (KR)

(72) Inventor: Jeong Beom Kim, Gimhae-si (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 963 days.

(21) Appl. No.: 15/120,192

(22) PCT Filed: Mar. 9, 2015

(86) PCT No.: PCT/KR2015/002253
§ 371 (c)(1),
(2) Date: Aug. 19, 2016

(87) PCT Pub. No.: WO2015/133879
PCT Pub. Date: Sep. 11, 2015

(65) Prior Publication Data
US 2017/0058258 A1    Mar. 2, 2017

(30) Foreign Application Priority Data

Mar. 7, 2014    (KR) .................. 10-2014-0027245
Mar. 9, 2015    (KR) .................. 10-2015-0032322

(51) Int. Cl.
| | | |
|---|---|---|
| C12N 5/079 | (2010.01) | |
| A61K 35/30 | (2015.01) | |
| A61K 35/38 | (2015.01) | |
| C12N 15/85 | (2006.01) | |
| A61K 35/33 | (2015.01) | |
| A61K 35/28 | (2015.01) | |
| A61K 35/51 | (2015.01) | |
| G01N 33/50 | (2006.01) | |
| A61K 35/17 | (2015.01) | |
| A61K 38/17 | (2006.01) | |

(52) U.S. Cl.
CPC ............ *C12N 5/0622* (2013.01); *A61K 35/17* (2013.01); *A61K 35/28* (2013.01); *A61K 35/30* (2013.01); *A61K 35/33* (2013.01); *A61K 35/38* (2013.01); *A61K 35/51* (2013.01); *A61K 38/1709* (2013.01); *C12N 15/85* (2013.01); *G01N 33/5058* (2013.01); *C12N 2500/38* (2013.01); *C12N 2501/01* (2013.01); *C12N 2501/115* (2013.01); *C12N 2501/135* (2013.01); *C12N 2501/395* (2013.01); *C12N 2501/60* (2013.01); *C12N 2501/602* (2013.01); *C12N 2501/603* (2013.01); *C12N 2506/1307* (2013.01); *C12N 2510/00* (2013.01); *G01N 2333/4703* (2013.01); *G01N 2800/285* (2013.01)

(58) Field of Classification Search
None
See application file for complete search history.

(56) References Cited

U.S. PATENT DOCUMENTS

| | | |
|---|---|---|
| 2009/0047263 A1 | 2/2009 | Yamanaka et al. |
| 2012/0100615 A1 | 4/2012 | Tesar et al. |

FOREIGN PATENT DOCUMENTS

| | | |
|---|---|---|
| EP | 2954046 | 12/2015 |
| WO | 2013-139429 | 9/2013 |
| WO | 2014-124087 | 8/2014 |

OTHER PUBLICATIONS

Kim, J. et al., The EMBO J., 2015, vol. 34: pp. 2971-2983.*
Keller, AC., 'Direct Reprogramming of Neural Stem Cells into Oligodendrocyte Progenitors by Defined Factors', 2013.
Yang, N. et al., 'Generation of Oligodendroglial Cells by Direct Lineage Conversion', Nature Biotechnology, May 2013., vol. 31, No. 5, pp. 434-439.
Najm, FJ. et al., 'Transcription Factor-Mediated Reprogramming of Fibroblasts to Expandable, Myelinogenic Oligodendrocyte Progenitor Cells', Nature Biotechnology, May 2013., vol. 31, No. 5, pp. 426-433.
Ring, KL. et al., 'Direct Reprogramming of Mouse and Human Fibroblasts into Multipotent Neural Stem Cells with a Single Factor', Cell Stem Cell, Jul. 6, 2012., vol. 11, pp. 100-109.

(Continued)

*Primary Examiner* — Michael D Burkhart
(74) *Attorney, Agent, or Firm* — Lex IP Meister, PLLC

(57) ABSTRACT

The present invention relates to a composition for inducing direct transdifferentiation into oligodendrocyte progenitor cells (OPCs) from somatic cells, the composition containing at least one protein selected from the group consisting of direct transdifferentiation factors OCT4, SOX1, SOX2, SOX10, OLIG2, NKX2.2, and NKX6.2, a nucleic acid molecule coding the protein, or a vector including the nucleic acid molecule introduced thereinto; a pharmaceutical composition for preventing or treating spinal cord injuries or demyelination diseases; a cell therapy agent for preventing or treating spinal cord injuries or demyelination diseases; a cell therapy agent for treating spinal cord injuries or demyelination diseases; a composition for screening drugs for the treatment of spinal cord injuries or demyelination diseases; a 3D printing biomaterial composition for manufacturing artificial tissues for the treatment of spinal cord injuries or demyelination diseases; and a method for direct transdifferentiation into oligodendrocyte progenitor cells from somatic cells. According to the present invention, the oligodendrocyte progenitor cells are prepared from somatic cells through direct transdifferentiation, and thus can be favorably utilized for the treatment of spinal cord injuries and demyelination diseases.

5 Claims, 11 Drawing Sheets

(56) References Cited

OTHER PUBLICATIONS

Kim, JB. et al., 'Oct4-Induced Pluripotency in Adult Neural Stem Cells', Cell, Feb. 6, 2009., vol. 136, pp. 411-419.
Lee et al., 'Direct reprogramming of mouse fibroblasts into oligodendrocyte progenitor cells by defined transcription factors', May 14, 2013.
Lee et al., 'Direct conversion of mouse fibroblasts into oligodendrocyte progenitor cells by defined transcription factors', Jun. 12, 2013.
Wang, S. et al., "Human iPSC-Derived Oligodendrocyte Progenitor Cells Can Myelinate and Rescue a Mouse Model of Congenital Hypomyelination", Cell Stem Cell (2013) 12: 252-264 (Feb. 7, 2013).
Maire Cecile L. et al., "Gain-of-function of Olig transcription factors enhances oligodendrogenesis and myelination", Date Base Medline, US National Library of Medicine (NLM), Bethesda, MD, US, Sep. 2010, XP002776812.
EPO, Office Action of Supplementary European Search Report of EP15758550.6 dated Jan. 12, 2018.

* cited by examiner

COMPOSITION FOR INDUCING DIRECT TRANSDIFFERENTIATION INTO OLIGODENDROCYTE PROGENITOR CELLS FROM SOMATIC CELLS AND USE THEREOF

TECHNICAL FIELD

The present invention relates to a composition for inducing the direct transdifferentiation of somatic cells into induced oligodendrocyte progenitor cells (iOPCs), including, as an active ingredient, at least one protein selected from the group consisting of direct transdifferentiation factors OCT4, SOX1, SOX2, SOX10, OLIG2, NKX2.2, and NKX6.2, a nucleic acid molecule encoding the protein, or a vector having the nucleic acid molecule introduced thereto, and to a method for direct transdifferentiation of somatic cells into oligodendrocyte progenitor cells using the above composition. In addition, the present invention relates to a pharmaceutical composition, a cell therapy agent, a drug screening composition, or a 3D printing biomaterial composition for manufacturing artificial tissue, each of which includes oligodendrocyte progenitor cells induced by the above method for direct transdifferentiation of somatic cells into oligodendrocyte progenitor cells, thereby being suitable for use in the prevention or treatment of spinal cord injury or demyelination disease.

BACKGROUND ART

Oligodendrocytes originate from the neuroepithelium during the differentiation of glial-restricted precursors, known as oligodendrocyte progenitor cells. Oligodendrocyte progenitor cells are a type of neuroglial cell that is essential for the production of the myelin sheath in the central nervous system (CNS). Myelination enables neurons to maintain the action potential of electrical impulses through severed axons.

The dysfunction of oligodendrocytes is a disorder created by the loss of myelin sheath, and causes many neurodegenerative diseases, including multiple sclerosis, cerebral palsy, leukodystrophy, neuropathy, central pontine myelinolysis, and hypomyelination. In order to treat damaged oligodendrocytes, transplantation of oligodendrocyte progenitor cells, functioning to restore endogenous cells or to produce myelin sheath, into the central nervous system, is the fundamental method for treating myelin injury.

In this regard, transplantation of oligodendrocytes has been used to treat myelin injury, but is problematic because effective methods of differentiating oligodendrocytes are not readily available and because it is very difficult to obtain large amounts of oligodendrocytes.

Furthermore, although methods for differentiation of embryonic stem cells (ESCs) and induced pluripotent stem cells into oligodendrocytes have been devised, they suffer from low induction efficiency into cells of interest and the risk of forming tumors from the embryonic stem cells or pluripotent stem cells upon differentiation into specific cells.

In order to eliminate the risk of forming tumors, research is ongoing into the direct transdifferentiation of somatic cells into other types of somatic cells or multipotent stem cells, rather than via pluripotent stem cells. However, such a cell reprogramming mechanism is difficult to specifically prove, attributable to the excessively large number of genes involved in the induction procedure, and thus the technical level thereof that has been exhibited to date is negligible. Despite the establishment of a de-differentiation strategy, the development of technically simple and highly efficient methods must continue in order to real-world therapeutic applications thereof. Moreover, when the techniques developed thus are evaluated in terms of efficiency and safety, they are dissatisfactory. Furthermore, methods of preparing oligodendrocyte progenitor cells by expressing only a single gene from somatic cells have not yet been known.

To respond to such circumstances, the present inventors have ascertained that oligodendrocyte progenitor cells may be prepared from somatic cells through direct transdifferentiation using at least one gene selected from among direct transdifferentiation factors OCT4, SOX1, SOX2, SOX10, OLIG2, NKX2.2, and NKX6.2, without the risk of forming tumors, thus culminating in the present invention.

DISCLOSURE

Technical Problem

Accordingly, an object of the present invention is to provide a composition for inducing the direct transdifferentiation of somatic cells into oligodendrocyte progenitor cells, including, as an active ingredient, at least one protein selected from the group consisting of direct transdifferentiation factors OCT4, SOX1, SOX2, SOX10, OLIG2, NKX2.2, and NKX6.2, a nucleic acid molecule encoding the protein, or a vector having the nucleic acid molecule introduced thereto.

Another object of the present invention is to provide a pharmaceutical composition for the prevention or treatment of spinal cord injury or demyelination disease, a cell therapy agent for the prevention or treatment of spinal cord injury or demyelination disease, a drug screening composition for the treatment of spinal cord injury or demyelination disease, or a 3D printing biomaterial composition for manufacturing artificial tissue for the treatment of spinal cord injury or demyelination disease, each of which includes, as an active ingredient, at least one protein selected from the group consisting of direct transdifferentiation factors OCT4, SOX1, SOX2, SOX10, OLIG2, NKX2.2, and NKX6.2, a nucleic acid molecule encoding the protein, a vector having the nucleic acid molecule introduced thereto, or an oligodendrocyte progenitor cell induced through direct transdifferentiation.

Still another object of the present invention is to provide a method for the direct transdifferentiation of somatic cells into oligodendrocyte progenitor cells.

Technical Solution

In order to accomplish the above objects, the present invention provides a composition for inducing the direct transdifferentiation of a somatic cell into an oligodendrocyte progenitor cell, including, as an active ingredient, at least one protein selected from the group consisting of direct transdifferentiation factors OCT4, SOX1, SOX2, SOX10, OLIG2, NKX2.2, and NKX6.2, a nucleic acid molecule encoding the protein, or a vector comprising the nucleic acid molecule.

In addition, the present invention provides an oligodendrocyte progenitor cell induced through direct transdifferentiation by introducing at least one protein selected from the group consisting of direct transdifferentiation factors OCT4, SOX1, SOX2, SOX10, OLIG2, NKX2.2, and NKX6.2, a nucleic acid molecule encoding the protein, or a vector comprising the nucleic acid molecule, to a somatic cell.

In addition, the present invention provides a pharmaceutical composition for the prevention or treatment of spinal cord injury or demyelination disease, including, as an active ingredient, at least one protein selected from the group consisting of direct transdifferentiation factors OCT4, SOX1, SOX2, SOX10, OLIG2, NKX2.2, and NKX6.2, a nucleic acid molecule encoding the protein, a vector comprising the nucleic acid molecule, or an oligodendrocyte progenitor cell induced through direct transdifferentiation.

In addition, the present invention provides a cell therapy agent for the prevention or treatment of spinal cord injury or demyelination disease, including, as an active ingredient, at least one protein selected from the group consisting of direct transdifferentiation factors OCT4, SOX1, SOX2, SOX10, OLIG2, NKX2.2, and NKX6.2, a nucleic acid molecule encoding the protein, a vector comprising the nucleic acid molecule, or an oligodendrocyte progenitor cell induced through direct transdifferentiation.

In addition, the present invention provides a composition for screening a drug for the treatment of spinal cord injury or demyelination disease, including, as an active ingredient, at least one protein selected from the group consisting of direct transdifferentiation factors OCT4, SOX1, SOX2, SOX10, OLIG2, NKX2.2, and NKX6.2, a nucleic acid molecule encoding the protein, a vector comprising the nucleic acid molecule, or an oligodendrocyte progenitor cell induced through direct transdifferentiation.

In addition, the present invention provides a 3D printing biomaterial composition (a biomaterial composition for 3D printing) for manufacturing artificial tissue for the treatment of spinal cord injury or demyelination disease, including, as an active ingredient, at least one protein selected from the group consisting of direct transdifferentiation factors OCT4, SOX1, SOX2, SOX10, OLIG2, NKX2.2, and NKX6.2, a nucleic acid molecule encoding the protein, a vector comprising the nucleic acid molecule, or an oligodendrocyte progenitor cell induced through direct transdifferentiation.

In addition, the present invention provides a method for direct transdifferentiation of a somatic cell into an oligodendrocyte progenitor cell, including introducing at least one protein selected from the group consisting of direct transdifferentiation factors OCT4, SOX1, SOX2, SOX10, OLIG2, NKX2.2, and NKX6.2, a nucleic acid molecule encoding the protein, or a vector comprising the nucleic acid molecule, to the somatic cell.

Advantageous Effects

According to the present invention, a composition for inducing the direct transdifferentiation of somatic cells into oligodendrocyte progenitor cells using at least one gene selected from among direct transdifferentiation factors OCT4, SOX1, SOX2, SOX10, OLIG2, NKX2.2, and NKX6.2 can be provided. In addition, the above composition can be effectively utilized to prepare oligodendrocyte progenitor cells from somatic cells, thereby treating spinal cord injury and demyelination disease.

DESCRIPTION OF DRAWINGS

Throughout the drawings, "iOPC-C1" and "iOPC-C2" respectively designate Clone 1 and Clone 2 of oligodendrocyte progenitor cells prepared according to the present invention.

BEST MODE

Figure 1A:
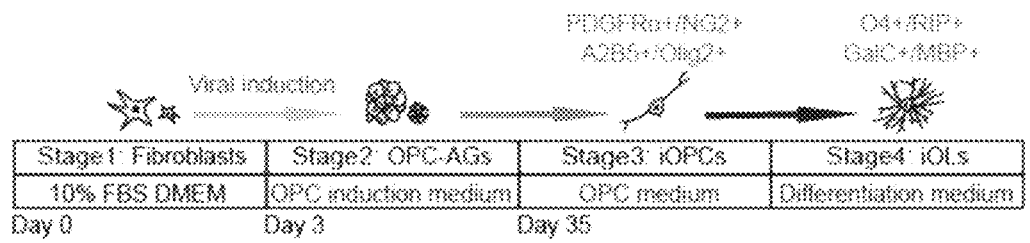
FIG. 1a is schematic illustration of the process of generating OCT4-induced iOPCs from fibroblasts.

In a specific embodiment of the present invention, in order to determine whether induced oligodendrocyte progenitor cells (iOPCs) may be generated using at least one gene selected from among direct transdifferentiation factors OCT4, SOX1, SOX2, SOX10, OLIG2, NKX2.2, and NKX6.2, somatic cells were separated and infected with retrovirus encoding a gene transcription factor for a direct transdifferentiation factor, thereby generating iOPCs (Test Result 1).

In another embodiment, the immature state of prepared iOPCs, as the precursor, was verified through immunocytochemistry and double staining. Consequently, the self-renewing capacity of the precursor and the growth rate of 31 passages or more were verified (Test Result 2).

Also, differentiation was induced to evaluate the differentiation capacity of generated iOPCs. Consequently, they were able to differentiate into mature oligodendrocytes or astrocytes (Test Result 3).

In still another embodiment of the present invention, total gene expression profiles of generated iOPCs and OPCs were compared. Consequently, the total gene expression profiles of iOPCs and OPCs were found to be similar, indicating that generated iOPCs were responsible for the functions of OPCs (Test Result 4).

Furthermore, in the present invention, iOPCs were transplanted into rats, the spinal cord of which was injured in vivo in order to evaluate the effects thereof on such spinal cord injury. Consequently, the injured spinal cord tissue was significantly alleviated, and myelination was restored without the generation of tumors.

Hereinafter, a detailed description will be given of the present invention.

The present invention addresses a composition for inducing the direct transdifferentiation of somatic cells into oligodendrocyte progenitor cells, including, as an active ingredient, at least one protein selected from the group consisting of direct transdifferentiation factors such as OCT4, SOX1, SOX2, SOX10, OLIG2, NKX2.2, and NKX6.2, a nucleic acid molecule encoding the protein, or a vector having the nucleic acid molecule introduced thereto.

The OCT4 (octamer-binding transcription factor 4) protein is known to be a POU5F1 protein, and is encoded by a POU5F1 gene. OCT4 is a homeodomain transcription factor in the POU family. Although the OCT4 protein is known to be associated with the self-renewal of undifferentiated embryonic stem cells, contents concerning the direct transdifferentiation of somatic cells into oligodendrocyte progenitor cells are not known at all. The gene sequence of OCT4 is registered with NCBI Registration Nos. NM_014209 and NM_013633.3.

SOX1 is a transcription factor in the SOX protein family, and is registered with NCBI Registration Nos. NM_005986.2 and NM_009233.3.

SOX2 is a transcription factor in the SOX protein family, and is registered with NCBI Registration Nos. NM_003106.3 and NM_011443.3.

SOX10 is a transcription factor in the SOX protein family, and is registered with NCBI Registration Nos. NM_006941.3 and NM_011437.1.

OLIG2 is a transcription factor in the OLIG protein family, and is registered with NCBI Registration Nos. NM_005806.3 and NM_016967.2.

NKX2.2 is a homeodomain transcription factor in the NK2 family, and is registered with NCBI Registration Nos. NM_002509.3 and NM_001077632.1.

NKX6.2 is a homeodomain transcription factor in the NK2 family, and is registered with NCBI Registration Nos. NM_177400.2 and NM_183248.3.

In the present invention, OCT4, SOX1, SOX2, SOX10, OLIG2, NKX2.2, and NKX6.2 genes may be provided in the form of a protein or a nucleic acid encoding the protein, and the protein may include any protein derived from humans or animals, such as mice, horses, sheep, pigs, goats, camels, antelopes, and dogs. Also, OCT4, SOX1, SOX2, SOX10, OLIG2, NKX2.2, and NKX6.2 proteins used in the present invention include not only proteins having wild-type amino acid sequences but also protein variants of individual genes.

The term "protein variant" refers to a protein, at least one amino acid residue of which differs from the native amino acid sequence, resulting from deletion, insertion, non-conservative or conservative substitution, or combinations thereof. The variant may be a functional equivalent that shows the same biological activity as a native protein, may be a variant in which physical and chemical properties of a protein are modified as necessary, or may be a variant the structural stability of which is increased under certain physical or chemical conditions, or the physiological activity of which is increased.

Also, a nucleic acid encoding the protein may have a base sequence encoding the wild-type protein or the variant-type protein, and may be mutated by subjecting at least one base to substitution, deletion, insertion, or combinations thereof. Also, it may be prepared via extraction from nature or using a chemical synthesis method. The nucleic acid having the base sequence encoding the protein may be a single chain or a double chain, and may be a DNA molecule (genomic DNA, cDNA) or an RNA molecule.

In an embodiment of the present invention, the nucleic acid molecule encoding the OCT4, SOX1, SOX2, SOX10, OLIG2, NKX2.2, or NKX6.2 protein may be a vector that expresses proteins by including the nucleic acids that encode each protein.

As used herein, the term "vector" refers to an expression vector that is able to express a protein of interest in a host cell, and may indicate a gene construct including an essential regulatory element that is operably linked to express a gene insert.

In the present invention, the vector may include a signal sequence or a reader sequence for membrane targeting or secretion, in addition to the expression regulatory element, such as a promoter, an operator, an initiation codon, a termination codon, a polyadenylation signal, or an enhancer, and may be variously manufactured so as to be adapted for some purpose. The promoter of the vector may be constructive or inductive. Furthermore, the expression vector includes a selective marker for selecting a host cell containing the vector, and a replicable expression vector includes a replication origin. The vector may be self-replicating, or may be integrated into the host DNA.

Figure 5:
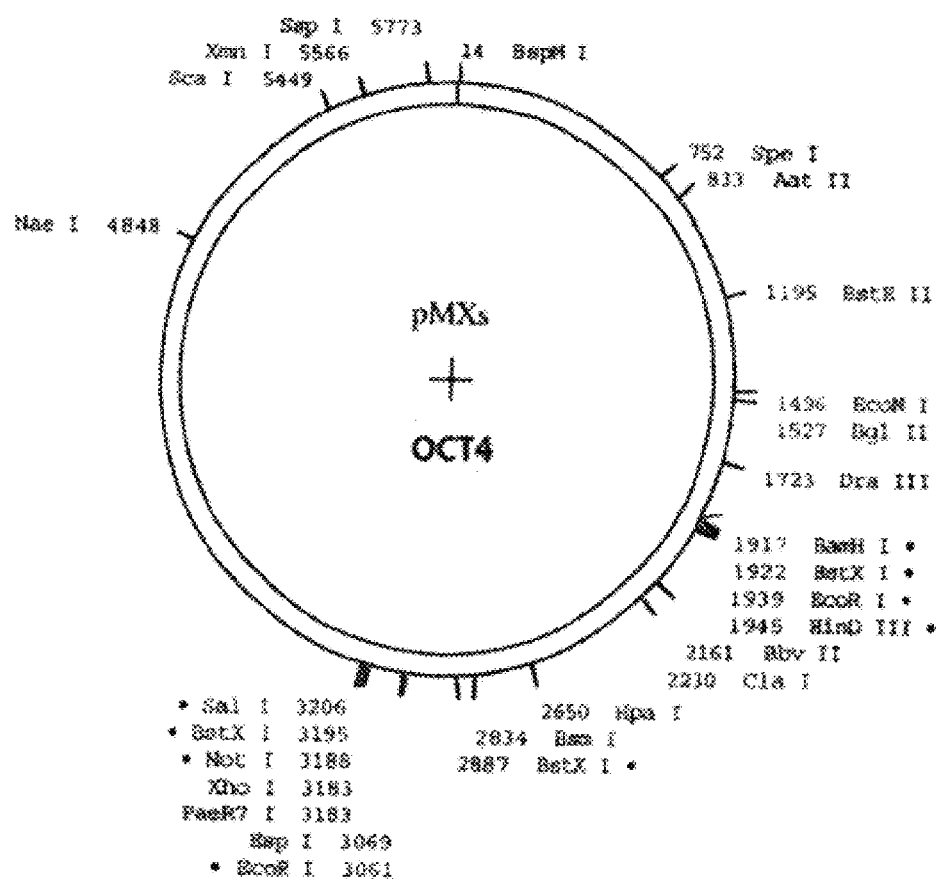
FIG. 5 illustrates the cleavage map of a pMX retroviral vector.

The vector may include a plasmid vector, a cosmid vector, a viral vector, and an episomal vector. Preferably useful is a viral vector. Examples of the viral vector may include, but are not limited to, a lentiviral vector, and a vector derived from Retrovirus, for example, HIV (Human Immunodeficiency Virus), MLU (Murine Leukemia Virus), ASLV (Avian Sarcoma/Leukosis), SNV (Spleen Necrosis Virus), RSV (Rous Sarcoma Virus), MMTV (Mouse Mammary Tumor Virus), Adenovirus, Adeno-associated virus, Herpes simplex virus, etc. Such a vector system is used to induce direct transdifferentiation through the over-expression of genes associated with specific cells in the vector delivered to somatic cells. Regardless of the vector system that is used, the effects of the present invention may be manifested. In a specific embodiment of the present invention, a pMX-based retroviral vector for expressing OCT4 may be used (FIG. 5).

Also, the nucleic acid encoding the protein may be transferred or introduced into the cells using any process known in the art, for example, using a vector-type naked DNA, or using a liposome, a cationic polymer, etc. The liposome is a phospholipid membrane obtained through mixing with cationic phospholipids such as DOTMA or DOTAP for gene delivery. When a cationic liposome and an anionic nucleic acid are mixed at a predetermined ratio, a nucleic acid-liposome complex may be formed, and may thereby be introduced into the cells.

Specifically in the present invention, the nucleic acid molecule encoding the protein is contained in the vector and virus manufactured so as to express each gene by transforming and infecting the viral vector, which includes the nucleic acid encoding the protein, into packaging cells, and may be thereby introduced into somatic cells. Examples of the virus may include, but are not limited to, Retrovirus, Adenovirus, Adeno-associated virus, Herpes simplex virus, etc.

As used herein, the term "somatic cell" refers to any cell other than a germ cell. Examples of somatic cells may be one selected from the group consisting of fibroblasts, muscle cells, nerve cells, gastric mucosal cells, goblet cells, G cells, pericytes, astrocytes, B cells, blood cells, epithelial cells, neural stem cells, hematopoietic stem cells, mesenchymal stem cells, cord blood stem cells, and the like. However, direct transdifferentiation may be applied regardless of the specific kind of tissue cell, so long as it starts from somatic cells, and the present invention is not limited to the above examples of somatic cells. In a specific embodiment of the present invention, skin fibroblasts are used.

As used herein, the term "oligodendrocyte progenitor cell" refers to a subtype of glial cell in the central nervous system. Such cells are a precursor of oligodendrocytes and are able to differentiate into neurons and astrocytes. Also, in the present invention, "iOPCs" designate induced oligodendrocyte progenitor cells, for example, induced oligodendrocyte progenitor cells prepared from somatic cells through direct differentiation according to the method of the present invention.

In addition, the present invention addresses oligodendrocyte progenitor cells induced through direct transdifferentiation by introducing somatic cells with at least one protein selected from the group consisting of direct transdifferentiation factors OCT4, SOX1, SOX2, SOX10, OLIG2, NKX2.2, and NKX6.2, a nucleic acid molecule encoding the protein, or a vector having the nucleic acid molecule introduced thereto.

In addition, the present invention addresses a pharmaceutical composition for the prevention or treatment of spinal cord injury or demyelination disease, including, as an active ingredient, at least one protein selected from the group consisting of direct transdifferentiation factors OCT4, SOX1, SOX2, SOX10, OLIG2, NKX2.2, and NKX6.2, a nucleic acid molecule encoding the protein, a vector having the nucleic acid molecule introduced thereto, or an oligodendrocyte progenitor cell induced through direct transdifferentiation.

In addition, the present invention addresses a cell therapy agent for the prevention or treatment of spinal cord injury or demyelination disease, including, as an active ingredient, at least one protein selected from the group consisting of direct transdifferentiation factors OCT4, SOX1, SOX2, SOX10, OLIG2, NKX2.2, and NKX6.2, a nucleic acid molecule encoding the protein, a vector having the nucleic acid molecule introduced thereto, or an oligodendrocyte progenitor cell induced through direct transdifferentiation.

In addition, the present invention addresses a drug screening composition for the treatment of spinal cord injury or demyelination disease, including, as an active ingredient, at least one protein selected from the group consisting of direct transdifferentiation factors OCT4, SOX1, SOX2, SOX10, OLIG2, NKX2.2, and NKX6.2, a nucleic acid molecule encoding the protein, a vector having the nucleic acid molecule introduced thereto, or an oligodendrocyte progenitor cell induced through direct transdifferentiation.

Spinal cord injury includes any case where the spinal cord, which is a portion of the central nervous system, is injured due to external or internal causes and thus does not perform its function, and may be caused by, for example, external injury, such as commotion, compression, or contusion, but the present invention is not limited thereto. Moreover, when the spinal cord, which is a portion of the central nervous system, does not perform its function, a variety of symptoms, such as thermoregulatory dysfunction, diaphragmatic paralysis, intercostal paralysis, perspiration, motor paralysis, sensory paralysis, dysuria, pressure sores, heterotopic ossification, fasciculation, etc., may appear.

Also, demyelination disease means any disease associated with the myelin sheath of the nerves, and examples thereof include, but are not limited to, multiple sclerosis, cerebral palsy, leukodystrophy, neuropathy, central pontine myelinolysis, and hypomyelination.

As used herein, the term "cell therapy agent" refers to a medicine (US FDA-regulated) used for the purpose of treatment, diagnosis or prevention of diseases with cells and tissues manufactured through culturing and specialized tasks after separation from human beings, especially a medicine used for the purpose of treatment, diagnosis or prevention of diseases by proliferating or screening autologous, allogeneic or xenogeneic living cells in vitro or otherwise changing the biological characteristics of cells in order to restore the functions of cells or tissues.

The method of determining the reactivity of the induced oligodendrocyte progenitor cells according to the present invention in the presence and absence of a therapeutic candidate material for treating spinal cord injury or demyelination disease may be usefully employed in screening a therapeutic agent for treating spinal cord injury or demyelination disease. For example, the induced oligodendrocyte progenitor cells according to the present invention are nerve cells, which are regarded as important in the treatment of and recovery from demyelination disease, and may be used to evaluate the toxicity or efficacy of the candidate material.

The toxicity may be evaluated based on methods of determining toxicity typically used in the art, such as methods of measuring $IC_{50}$ of induced oligodendrocyte progenitor cells according to the present invention, or depending on whether the differentiation of induced oligodendrocyte progenitor cells according to the present invention into oligodendrocytes in the presence and absence of a therapeutic candidate material of the invention is inhibited. Also, the efficacy may be evaluated based on methods of determining treatment effects on demyelination disease in the art, such as methods of promoting myelination, or depending on whether the differentiation of induced oligodendrocyte progenitor cells according to the present invention into oligodendrocytes in the presence and absence of a therapeutic candidate material of the invention is promoted.

In addition, the present invention addresses a 3D printing biomaterial composition for manufacturing artificial tissue for the treatment of spinal cord injury or demyelination disease, including, as an active ingredient, at least one protein selected from the group consisting of direct transdifferentiation factors OCT4, SOX1, SOX2, SOX10, OLIG2, NKX2.2, and NKX6.2, a nucleic acid molecule encoding the protein, a vector having the nucleic acid molecule introduced thereto, or an oligodendrocyte progenitor cell induced through direct transdifferentiation.

In addition, the present invention addresses a method for the direct transdifferentiation of somatic cells into oligodendrocyte progenitor cells, including introducing somatic cells with at least one protein selected from the group consisting of direct transdifferentiation factors OCT4, SOX1, SOX2, SOX10, OLIG2, NKX2.2, and NKX6.2, a nucleic acid molecule encoding the protein, or a vector having the nucleic acid molecule introduced thereto.

More specifically, the method includes: culturing somatic cells in a culture medium, transfecting the cultured somatic cells with a gene-inserted vector, and culturing the infected somatic cells under culture conditions for inducing direct transdifferentiation.

The culture medium used for culturing the somatic cells includes any medium typically useful in the culture of somatic cells in the art. The culture medium usually contains a carbon source, a nitrogen source, and small amounts of elements. In a specific embodiment of the present invention, a culture medium containing protamine sulphate is used.

Also, the culture conditions for inducing the direct transdifferentiation of somatic cells may include any culture medium typically used to induce direct transdifferentiation of somatic cells in the art. In a specific embodiment of the present invention, a culture medium containing N2-supplemented DMEM/F12, penicillin/streptomycin, 20 ng/ml PDGF-AA, and 10 ng/ml FGF-2 is used.

Through the introduction of somatic cells with the composition for inducing direct transdifferentiation according to the present invention, ectopic expression of the direct transdifferentiation factor may be induced. Here, ectopic expression is the expression of a gene in a tissue or cell where it is not normally expressed, or is the expression of a gene at a point in time at which it is not normally expressed. In a specific embodiment of the present invention, the composition for inducing direct transdifferentiation is introduced into the somatic cells, thereby inducing expression of the direct transdifferentiation factor in the somatic cells. Accordingly, oligodendrocyte progenitor cells may be prepared from the somatic cells.

The oligodendrocyte progenitor cells, prepared according to the present invention, play an essential role in myelination in the central nervous system, and are able to differentiate into oligodendrocytes, neurons or astrocytes, and thus may be applied to the prevention or treatment of disease caused by the loss of myelin sheath.

MODE FOR INVENTION

A better understanding of the present invention may be obtained through the following examples, which are set forth to illustrate, but are not to be construed as limiting the scope of the present invention. The examples of the present invention are provided to fully describe the present invention to those having ordinary knowledge in the art to which the present invention pertains.

Test Example 1. Generation of iOPCs

Skin fibroblasts were aliquoted in an amount of $3 \times 10^4$ cells on a gelatin-coated 6-well plate with 10% FBS culture medium. After one day, the fibroblasts were infected with a pMX retroviral vector for expressing OCT4 in a 6 µg/ml protamine sulfate-containing medium. 24 hr after infection, the viral supernatant was removed, and the medium was replaced with a new medium. On the $3^{rd}$ day after infection, the cells were transferred into a chemically modified OPC medium (N2-supplemented DMEM/F12, penicillin/streptomycin, 20 ng/ml PDGF-AA (Peprotech), 10 ng/ml FGF-2 (Peprotech)). 12 days after additional culture in the OPC medium, OPC-like aggregates were mechanically separated, and mature iOPCs were picked or were subcultured by trypsinization in the gelatin-coated plate.

Test Example 2. Differentiation of iOPCs (In Vitro)

In order to prepare mature oligodendrocytes, iOPCs were plated onto a PDL/laminin-coated 4-well plate with an OPC medium. On the next day, the medium was replaced with an oligodendrocyte differentiation medium 1 (N2-supplemented DMEM/F12, penicillin/streptomycin, 10 ng/ml FGF-2 (Peprotech), 10 mM forskolin (Sigma)), and then maintained for four to five days. After the first differentiation stage, the cells were treated with an oligodendrocyte differentiation medium 2 (30 ng/ml 3,3,5-tri-iodothyronine (T3; Sigma), 20 ng/ml ascorbic acid (AA; Sigma)).

Test Example 3. Retroviral Production

A pMX-based retroviral vector for expressing OCT4 was transfected into 293T cells (ATCC, CAT #. CRL-3216) using an X-tremeGENE9 DNA transfection reagent (Roche) as a VSV-G-like virus package. 48 hr after transfection, the virus-containing supernatant was collected and filtered with a 0.45 lam syringe filter, thus acquiring a virus.

Test Example 4. Quantitative Real-Time PCR

DNA-free total RNA was extracted using an RNeasy mini kit (Qiagen). A total of 500 ng of RNA per reaction was used to synthesize cDNA with SuperScript® III reverse transcriptase (Invitrogen). The synthesized cDNA had a total volume of 20 μL and was used as a template by LightCycler 480 SYBR Green I Mastermix (Roche). The OPC marker genes, pluripotent stem cells and neural markers were tested three times and normalized to housekeeping gene Gapdh. Gene expression was measured through Ct value calculation. All tests were performed according to the manufacturer's description.

Test Example 5. Immunocytochemistry

The cells were immobilized for 10 min in 4% para-formaldehyde and treated with 0.1% Triton X-100 for 10 min so as to be permeable. The cells were incubated in a 4% FBS blocking solution for 30 min and then further incubated in a primary antibody diluted with the blocking solution at room temperature for 1 hr: Oligo2 (Santacruz, 1:200), PDGFR-α (Abcam, 1:500), A2B5 (Millipore, 1:500), NG2 (Millipore, 1:200), O4 (Millipore, 1:400), RIP (DSHB, 1:200), GalC (Chemicon, 1:200), GFAP (Sigma, 1:500). After the primary antibody treatment, the cells were washed three times with PBST (0.05% tween20). A secondary antibody was diluted with PBS and incubated for 1 hr together with the cells (Alexa Fluor 488/568 anti-mouse IgG1, IgG3, IgM, anti-goat IgG (Invitrogen, 1:1000)). The nuclei were stained for 10 sec using Hoechst 33342 (Thermo). The primary antibodies used in the test are summarized in Table 1 below.

TABLE 1

| Antibody | Source | Isotype | Dilution | Localization |
| --- | --- | --- | --- | --- |
| Olig2 | Santacruz | Goat IgG | 1:200 | Nucleus |
| PDGFR-α | Abcam | Mouse IgG | 1:200 | Receptor |
| A2B5 | Millipore | Mouse IgM | 1:500 | Cell surface |
| NG2 | Millipore | Mouse IgG | 1:100 | Cell surface |
| O4 | Millipore | Mouse IgM | 1:200 | Cell surface |
| RIP | DSHB | Mouse IgG1 | 1:200 | Cell surface |
| MBP | Millipore | Mosue IgG2a | 1:100 | Myelin membrane |
| GalC | Millipore | Mosue IgG3 | 1:200 | Cytoplasm |
| GFAP | SIGMA | Mouse IgG1 | 1:500 | Cytoplasm |

Test Example 6. Preparation of Skin Fibroblasts

The skin fibroblasts were separated and cultured in an MEF medium (Dullbecco's modified Eagle's medium supplemented with 10% FBS, nonessential amino acids, L-glutamine, penicillin/streptomycin, mercaptoethanol) at 37° C. in a 5% $CO_2$ incubator.

Test Example 7. Characteristics of Fibroblasts Through RT-PCR and Immunocytochemistry 35 cycles of RT-PCR were performed using a Taq DNA polymerase recombinant (Invitrogen). For immunocytochemistry, the cells were immobilized for 10 min in para-formaldehyde in a 4% PBS (pH 7.4) and treated with 0.1% Triton X-100 for 10 min so as to be permeable. The cells were incubated in a 4% FBS blocking solution for 30 min and then further incubated in a primary antibody diluted with the blocking solution at room temperature for 1 hr: Oct4 (Santacruz, 1:200), Sox2 (Santacruz, 1:400), Olig2 (Santacruz, 1:200), Pax6 (DSHB, 1:200), O4 (Millipore, 1:400), RIP (DSHB, 1:200), GFAP (Sigma, 1:500). After the primary antibody treatment, the cells were washed and incubated in a secondary antibody for 1 hr (Alexa Fluor 488/568 anti-mouse IgG1, IgG3, IgM, anti-goat IgG (Invitrogen, 1:1000)). The nuclei were stained for 10 sec using Hoechst 33342 (Thermo).

Test Example 8. Silencing of OCT4 Transgene Through Quantitative Real-Time PCR

Total RNA was extracted using an RNeasy mini kit (Qiagen). A total of 500 ng of RNA per reaction was synthesized into cDNA with SuperScript® lift reverse transcriptase (Invitrogen). The synthesized cDNA had a total volume of 20 μL and was analyzed through real-time PCR using LightCycler 480 SYBR Green I Mastermix (Roche). The testing was repeated three times and normalization to the housekeeping gene GAPDH was carried out. Gene expression was measured through Ct value calculation.

Test Example 9. Microarray Analysis Technique

Through a microarray analysis technique, the total gene expression of fibroblasts, fibroblasts on the $3^{rd}$ day after OCT4 infection (fibroblasts-day3), fibroblasts on the $10^{th}$ day after OCT4 infection (fibroblasts-day10), a control (fibroblasts cultured in OPC medium without infection), iOPC-C1, and iOPC-C2 was profiled and compared with bona fide OPC samples of previously published data. Total RNA was separated using an RNeasy mini kit (Qiagen) according to the manufacturer's instructions. The sample was hybridized with Affymetrix array and normalized through calculation using an RMA (Robust Multi-array Analysis) algorithm. Data processing and graphics were executed using an internally developed MATLAB application. Hierarchical clustering of genes and samples was carried out through one minus correlation metric and the unweighted average distance (UPGMA) linkage method.

Test Example 10. Spinal Cord Injury and Transplantation

As a spinal cord injury model, a 6-week-old male rat was used, and the chest spine level 9(T9) of the spinal cord thereof was injured using an air punching device. One week after injury, the obtained iOPCs were labeled with DiI and injected at a concentration of $1 \times 10^5$ iOPCs/rat into the chest spine level 8(T8) and the chest spine level 10(T10) of the spinal cord through a stereotaxic method. Water and food were regularly fed to the rat and the bladder of the rat was massaged for urination. The animal testing was approved by the Animal Facility and the IBR Committee of the Ulsan National Institute of Science and Technology. The animal experimental procedure was based on the guidelines of the National Institute of Health for animal studies.

Test Example 11. Histological Process and Immunohistochemical Analysis 12 weeks after transplantation, the rat was anesthetized and perfused with PBS. The spinal cord was immobilized overnight with 4% para-formaldehyde and dehydrated in alcohol and xylene at stepwise concentrations. The tissue was placed in a paraffin block and consecutively sliced to a thickness of 4 μm in sagittal and coronal directions. The sliced portions were made permeable with 0.25% Triton X-100, and non-specific binding sites were blocked with a 10% blocking solution. For immunohistochemical analysis, the sliced portions were incubated with a primary antibody:

PDGFR-α (Abcam, 1:100), O4 (Millipore, 1:100), RIP (DSHB, 1:100), GFAP (Sigma, 1:100), MBP (Millipore, 1:100). Thereafter, the spinal cord was stained with a secondary antibody. The fluorescent images were visualized using an Olympus microscope, model IX81-ZDC.

Test Results

1. Preparation of iOPCs from Adult Fibroblasts using OCT4 Alone

Figure 1B:
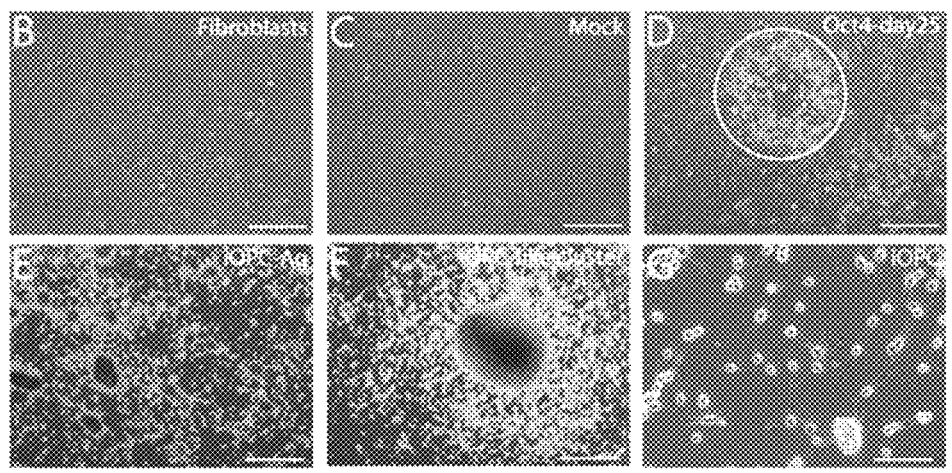
FIG. 1b is of phase-contrast microscope images illustrating changes during the gradual differentiation of fibroblasts into iOPCs, in which "B" shows uninfected fibroblasts, "C" shows a control, "D" shows fibroblast-OCT4 on the $25^{th}$ day, "E" shows an OCT4-induced fibroblast aggregate, "F" shows an iOPC-like colonies, and "G" shows the bipolar morphology of iOPCs, and scale bars of E and F are 500 μm, scale bars of B to D are 200 μm, and scale bars of G are 100 μm.
Figure 1C:
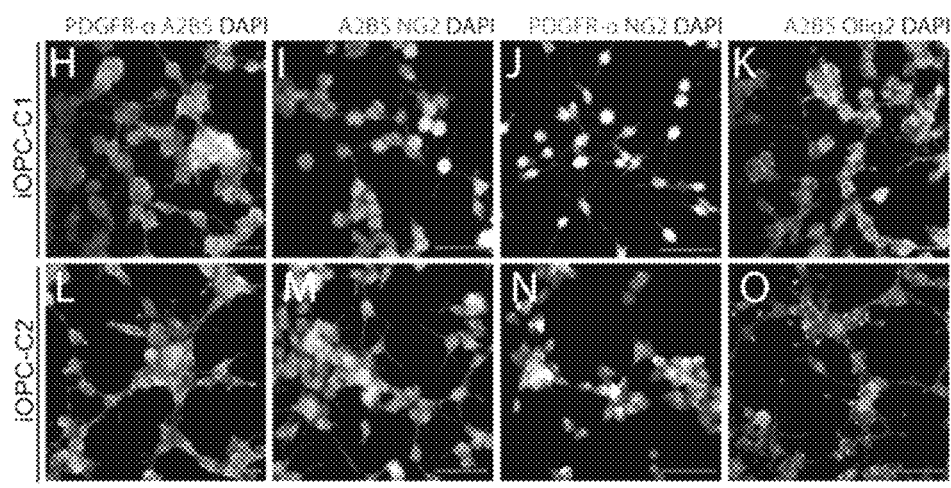
FIG. 1c illustrates the results of immunocytochemistry assay of OCT4-induced iOPC clones double-stained with iOPC-specific markers such as PDGFR-α, NG2, A2B5, and Olig2, in which scale bars are 125 μm.

In order to induce cell fate conversion into OPCs in the course of inducing the differentiation of FIG. 1a, skin fibroblasts were infected with a retrovirus encoding an OCT4 transcription factor. As illustrated in FIG. 1b, uninfected fibroblasts had typical fibroblast morphology before induction. The separated fibroblasts did not express pluripotent cell genes or nervous system genes, and pluripotent stem cell or nerve cell clustering could not be confirmed even through immunostaining. The fibroblasts were reduced in size and changed to a nerve cell-like shape from the $25^{th}$ day after the introduction of OCT4 to a glial cell induction medium, but the control cells having no OCT4 did not change (D and C of FIG. 1b). In order to increase the generation of cells such as iOPCs, they were cultured in a specific medium, which was supplemented with PDGF-AA, a growth factor essential for OPCs. 30 days after the introduction, cells having a nerve cell-like shape were mechanically separated and glial cells were continuously induced in a specific OPC medium. As a result, iOPC aggregates (iOPC-Ag) were observed 20 days after culture in the OPC medium (E of FIG. 1b). Next, when iOPC-Ag was transferred to a gelatin-coated plate, iOPC-like clusters were formed (F of FIG. 1b), and iOPC-like cells departed from the above clusters after attachment (G of FIG. 1b). It was confirmed using PCR that OCT4 genes were transferred to and integrated with the host DNA of iOPC. In order to verify silencing of the transferred genes, the mRNA level of OCT4 was measured using real-time PCR. Furthermore, iOPCs were subjected to cell fate conversion through viral induction, after which karyotypes of chromosomes thereof were maintained Thereby, OCT4 was proven to be suitable for the initial fate conversion from the fibroblasts into iOPCs.

2. Self-renewal of iOPCs induced by OCT4 and Characteristics of OPCs

In order to evaluate the lineages of iOPCs induced by OCT4 and the immature state thereof as a precursor, immunocytochemistry assay was performed using OPC markers such as PDGFR-α, NG2, A2B5 and Olig2. These markers were expressed in all iOPCs, and common expression of the markers was confirmed through double-immunostaining.

Figure 1D:
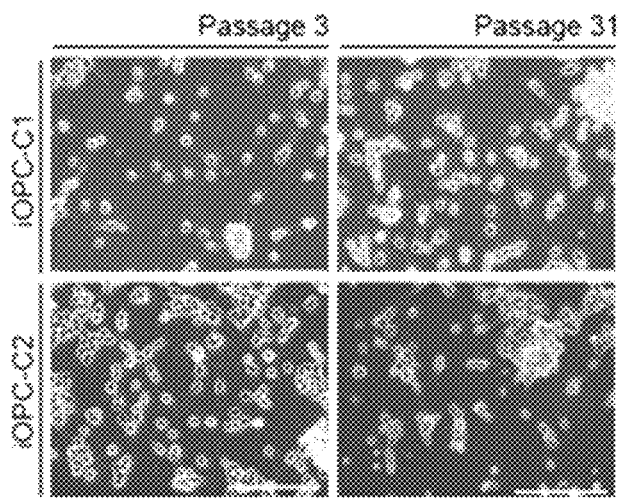
FIG. 1d illustrates phase-contrast microscope images of self-renewing iOPCs, in which scale bars are 100 μm.
Figure 1E:
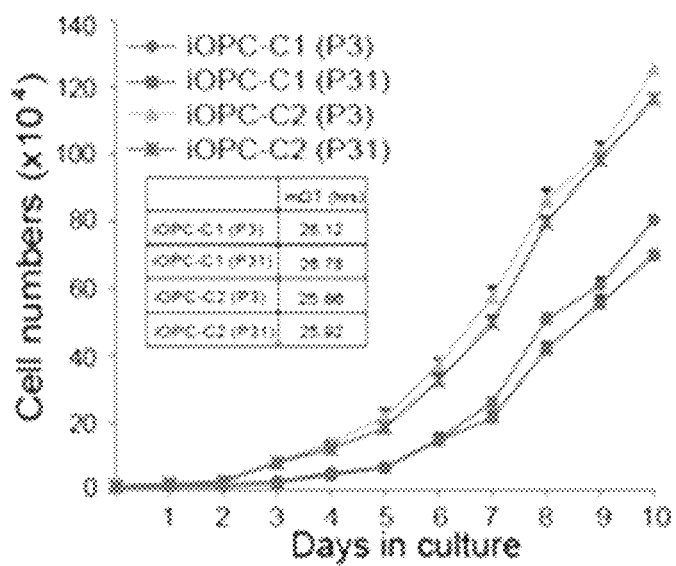
FIG. 1e illustrates the proliferation rates of iOPCs over time in initial passage (P3) and late passage (P31), in which data is represented by average±standard error.

Two iOPC clones that were stably uniformly proliferated were obtained. Both of the clones could be extended up to 31 passages or more, without changes in the characteristics or morphologies thereof (FIG. 1d). The growth characteristics were evaluated by measuring the average doubling time of iOPCs (FIG. 1e). The growth curve showed the self-renewal capacity of iOPCs. The growth rate was maintained up to a late passage number such as 31 passages or more.

Figure 2A:
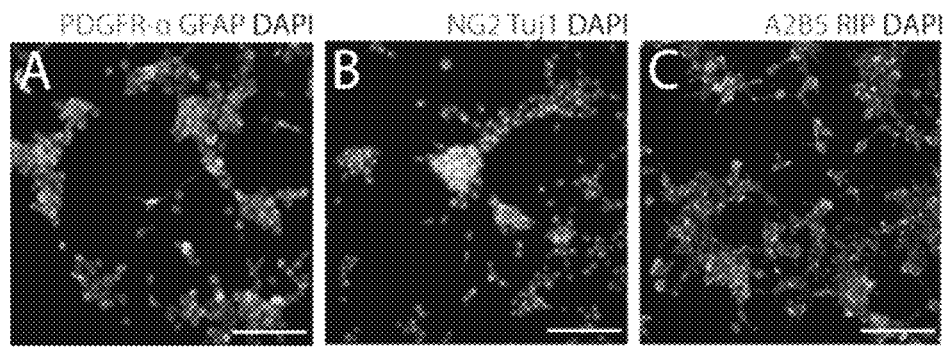
FIG. 2a illustrates immunocytochemistry images of undifferentiated iOPCs, in which "A" shows an image stained with PDGFR-α and GFAP, "B" shows an image stained with NG2 and Tuj1, and "C" shows an image stained with A2B5 and RIP, and scale bars are 250 μm.

3. Differentiation of Multipotent iOPCs as Glial-Restricted Stem Cells into Mature Oligodendrocytes and Astrocytes In order to evaluate the iOPC clone, which is a glial-restricted uniform precursor, the expression of GFAP (astrocyte), Tuj1 (immature neuron), and RIP (mature oligodendrocyte) markers in iOPCs was checked. GFAP positive astrocytes were not detected, or were seldom present, in undifferentiated iOPCs (A of FIG. 2a). In order to evaluate whether iOPCs were restricted to glial lineages, the cells were stained with a neuronal marker Tuj1, which is not expressed in undifferentiated iOPCs (B of FIG. 2a). Furthermore, RIP, serving as the late-stage oligodendrocyte marker, was not detected in undifferentiated iOPCs. Thereby, iOPCs were determined to be a homogeneous population (C of FIG. 2a).

Figure 2B:
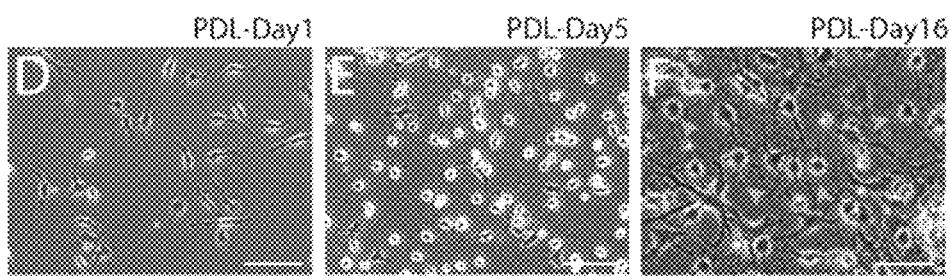
FIG. 2b is of phase-contrast microscope images illustrating changes in morphology during the in vitro differentiation of iOPCs, in which "D" shows the results on the $1^{st}$ day, "E" shows the results on the $5^{th}$ day, "F" shows the results on the $16^{th}$ day, the green arrow designates the oligodendrocyte, the red arrow designates the astrocyte, and scale bars are 100 μm.
Figure 2C:
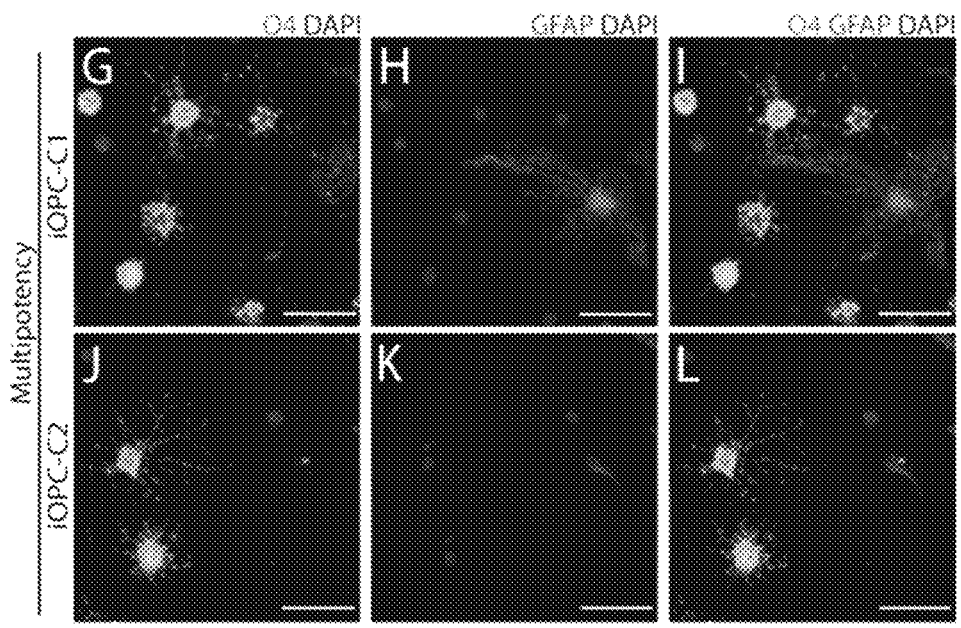
FIG. 2c illustrates the coexistence of O4+ oligodendrocyte (green) and GFAP+astrocyte (red) showing the multipotency of iOPCs after differentiation, in which scale bars are 125 μm.

Also, iOPCs are multipotent stem cells able to differentiate into glial lineage cells. In order to evaluate the multipotency of iOPCs, the differentiation of iOPCs was induced, and whether iOPCs were able to differentiate into mature oligodendrocytes or other glial lineage cells was checked. The undifferentiated iOPCs were plated onto a PDL/Laminin-coated plate with a differentiation medium supplemented with forskolin, ascorbic acid and T3, suitable for promoting the maturation of oligodendrocytes, and were then immediately changed (D of FIG. 2b). For five days after differentiation, the shape of the cells was converted into a gradually flat shape with small branches (E of FIG. 2b). The mature shape of oligodendrocytes was further observed until 16 days, and they were observed to be present together with differentiated astrocytes (F of FIG. 2b). After differentiation, the cells were stained with the oligodendrocyte marker O4 and the astrocyte marker GFAP, whereby the oligodendrocytes were observed to be present together with astrocytes (G to L of FIG. 2c). However, the likelihood of differentiation of iOPCs into oligodendrocytes may vary depending on the kind of transcription factor that is used, and the efficiency thereof is relatively low. To evaluate the differentiation efficiency of OCT4-iOPCs, they were stained with O4, GFAP, Tuj1, and A2B5, and proportion of iOPCs was assayed after differentiation, and the extent of differentiation was evaluated during the maturation. Moreover, iOPCs appeared to be restricted to glial cells when induced under conditions appropriate for inducing astrocytes and neurons. Although iOPCs efficiently differentiated into astrocytes, they did not differentiate into Tuj1 positive neurons. Based on these results, glial-restricted iOPCs were proven to exhibit multipotency for differentiation not only into astrocytes but also into oligodendrocytes.

Figure 2D:
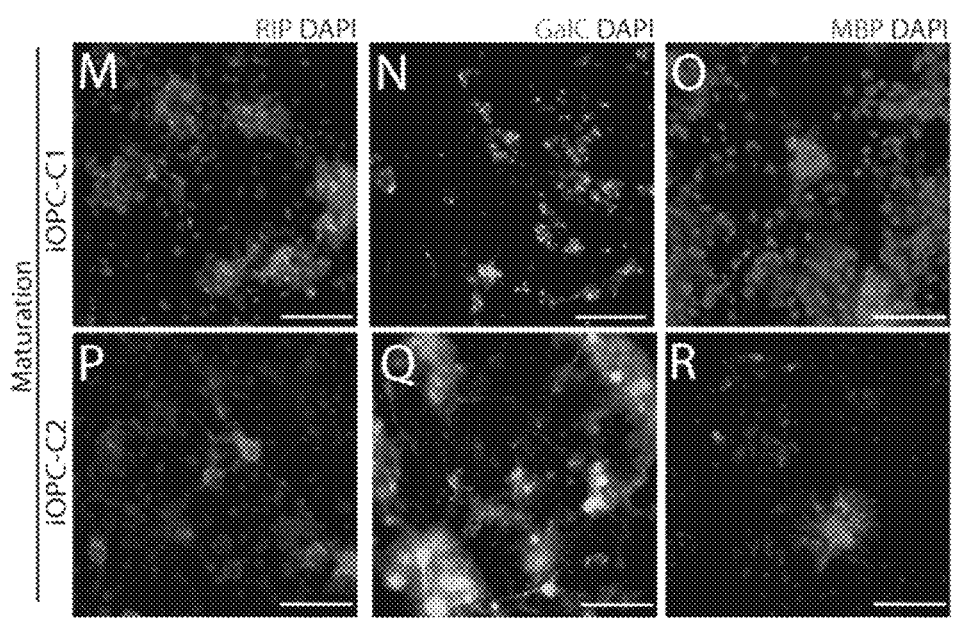
FIG. 2d illustrates the immunocytochemistry images of oligodendrocytes, which express mature oligodendrocyte markers, 30 days after differentiation, in which "M" and "P" show RIP expression, "N" and "Q" show GalC expression, "O" and "R" show MBP expression, and scale bars are 125 μm.

When iOPCs completely differentiated into late-stage mature oligodendrocytes, undifferentiated iOPCs did not express RIP (C of FIG. 2a), but expressed protein markers such as RIP, GalC, and MBP (M to R of FIG. 2d). Moreover, homogenous OCT4-iOPCs were proven to have multipotency for differentiation into oligodendrocytes.

4. Total Gene Profile Expression of iOPCs and OPCs

Figure 3A:
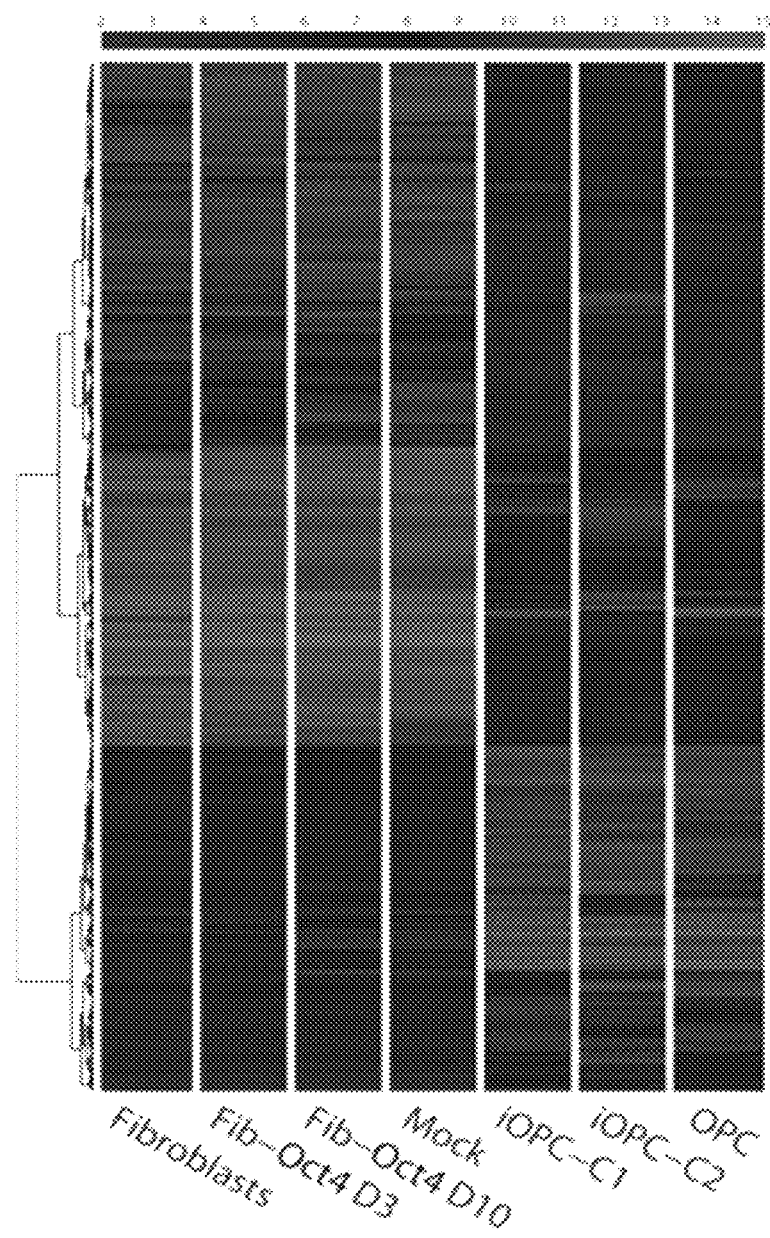
FIG. 3a illustrates the heatmap results of microarray analysis for the total gene expression of OCT4-induced iOPCs, in which "Fibroblasts" show fibroblasts, "Fib-OCT4 D3" shows fibroblasts on the $3^{rd}$ day during the differentiation induction by OCT4, "Fib-OCT4 D10" shows fibroblasts on the $10^{th}$ day during the differentiation induction by OCT4, "Mock" shows a control, and "wtOPC" shows OPCs derived from pluripotent stem cells.
Figure 3B:
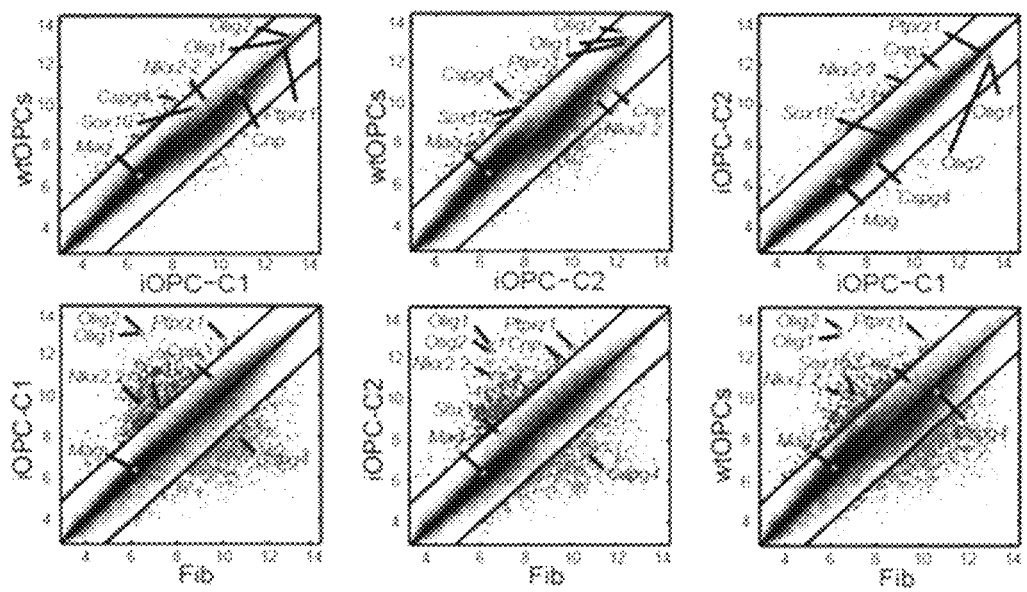
FIG. 3b illustrates scatter plots that compare total gene expression, showing correlations between fibroblasts and OPCs, fibroblasts and iOPC-C1, fibroblasts and iOPC-C2, iOPC-C1 and OPCs, iOPC-C2 and OPCs, and iOPC-C1 and iOPC-C2, in which the black line designates a boundary having two-fold gene expression changes between the coupled samples, and the gene expression level is represented by a log 2 value.
Figure 3C:
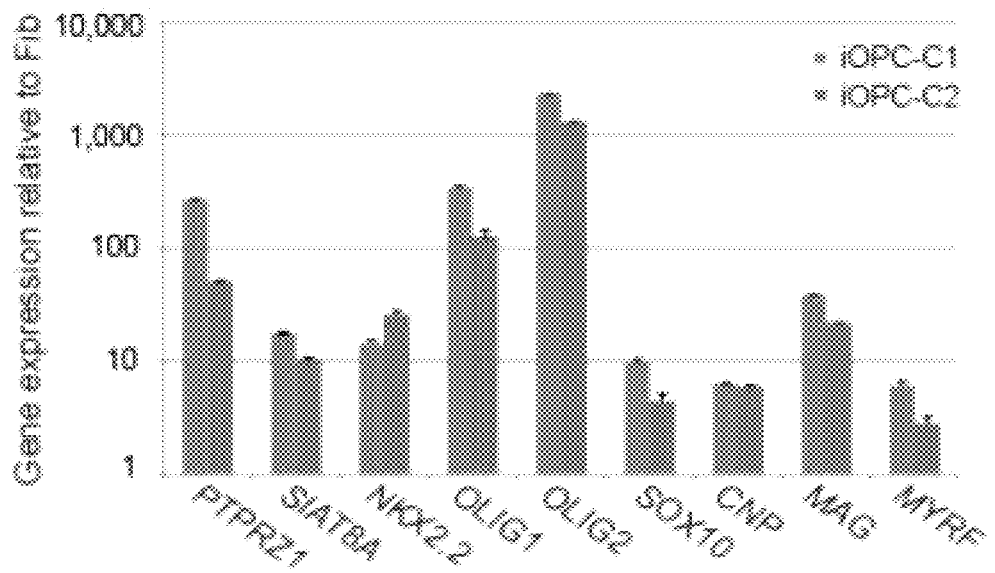
FIG. 3c illustrates the results of quantitative RT-PCR of OCT4-induced OPCs for gene expression of OPC-based markers and oligodendrocyte markers, in which the graph is shown in log 2 fold change normalized to GAPDH.
Figure 3D:
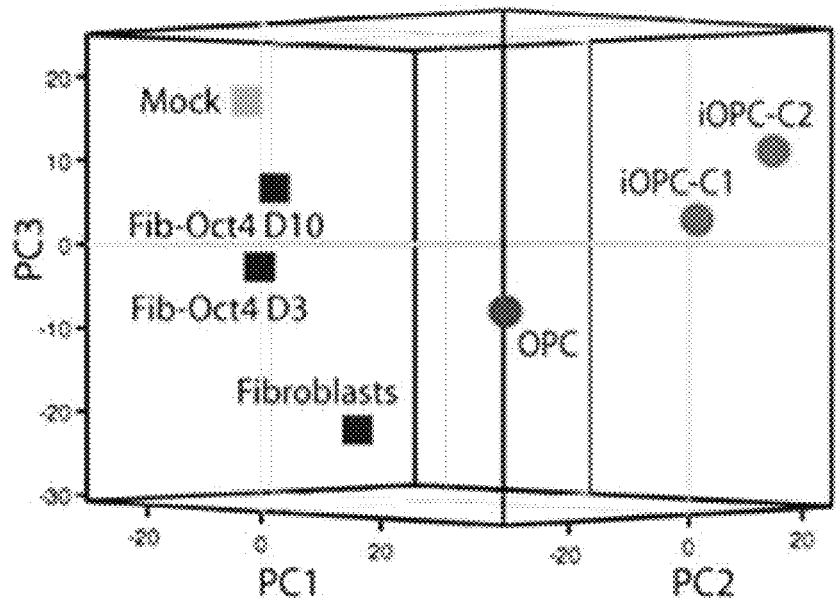
FIG. 3d illustrates the 3D analytical results of principal components, in which the first principal component (PC1) constitutes 64% of gene expression variability, the second principal component (PC2) constitutes 14% of the variability, and the third principal component (PC3) constitutes 8.3% of the variability.
Figure 3E:
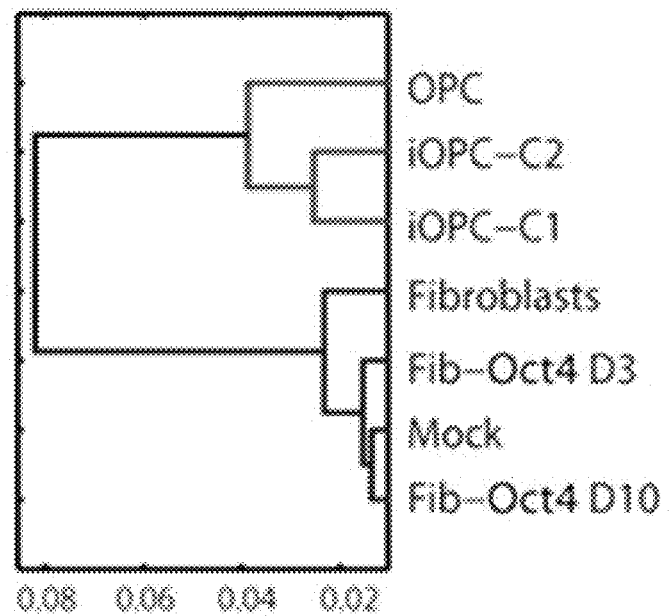
FIG. 3e illustrates the hierarchical clustering results of total gene expression, in which changes in gene expression are checked after OCT4 induction based on the results of microarray analysis, and the development of oligodendrocytes and neurons is related with genes that are highly expressed in iOPCs, compared to the fibroblasts.

In order to evaluate the extent of total gene expression of fibroblasts and iOPCs, a microarray analysis process was performed. The gene expression patterns of two established iOPC clones were very similar to OPCs induced from pluripotent stem cells (FIG. 3a). In contrast, the total gene expression had an opposite pattern in fibroblasts and control (Mock) (fibroblasts cultured in the OPC medium without OCT4 induction). Furthermore, there were no special changes in fibroblasts cultured only in the OPC medium without OCT4 induction. Thereby, OCT4 was essential for cell fate conversion into iOPCs. Through Pairwise scatter plot of the microarray data, the similarity between fibroblasts and iOPCs and the similarity between OPCs (bona fide) and iOPCs were verified (FIG. 3b). Through 3D PCA analysis and hierarchical clustering, iOPCs and OPCs (bona fide) were proven to be closely related to each other (FIGS. 3d and 3e), compared to the fibroblasts. Next, OPC-specific gene expression was confirmed using real-time PCR (FIG. 3c). In accordance with the microarray data, iOPCs expressed a high level of mRNA of OPC-specific genes such as PTPRZ1, SIAT8A, OLIG2, OLIG1, SOX10, NKX2.2, MAG, MYRF and CNP. In order to detect genes that were highly expressed after conversion, 68 genes associated with the development of oligodendrocytes and nervous system cells, the expression of which was increased in iOPCs compared to the fibroblasts, were identified.

5. Enhancement of Restoration of Spinal Cord Injured Rat by iOPCs (in vivo)

Figure 4A:
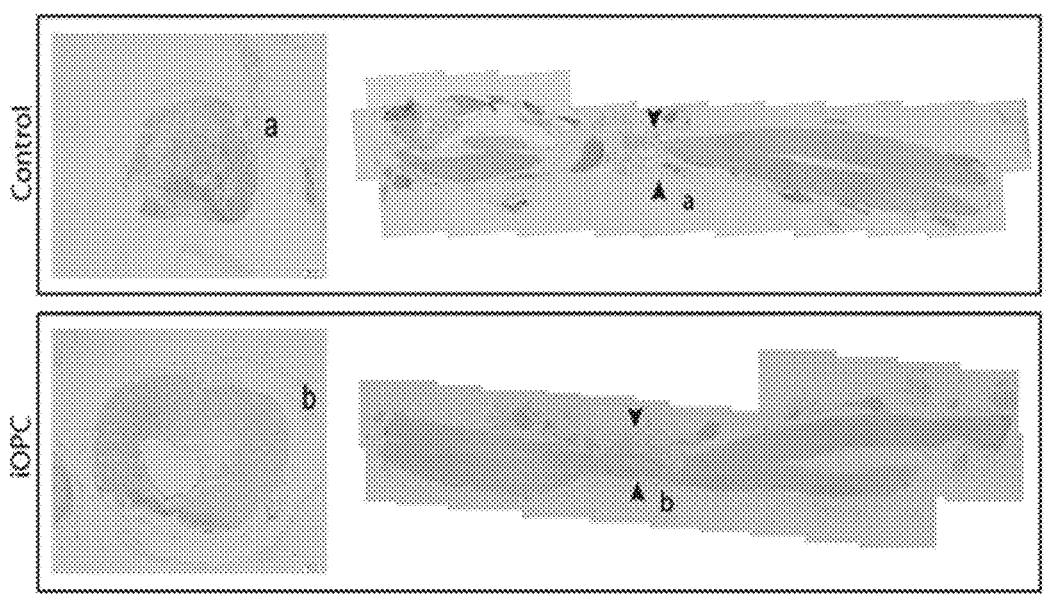
FIG. 4a illustrates images of the spinal cord of a rat stained by H&E, 12 weeks after transplantation into an injured portion, in which scale bars are 200 μm.
Figure 4B:
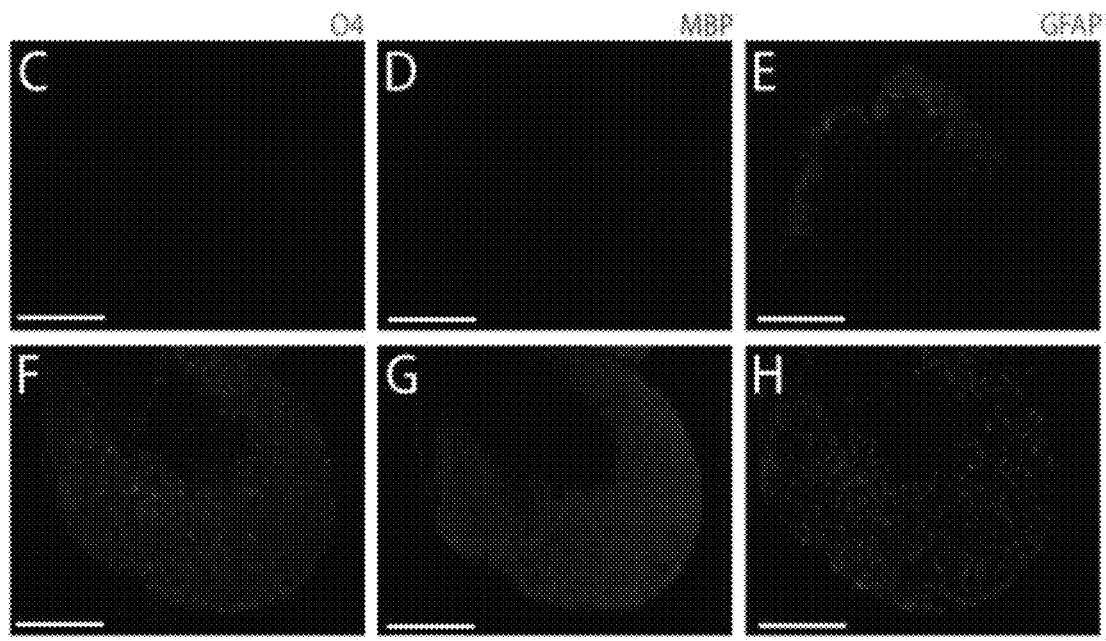
FIG. 4b illustrates the results of immunohistochemistry analysis of the injured spinal cord, in which "C" and "F" are stained with O4, "D" and "G" are stained with MBP, and "E and H" are stained with GFAP.
Figure 4C:
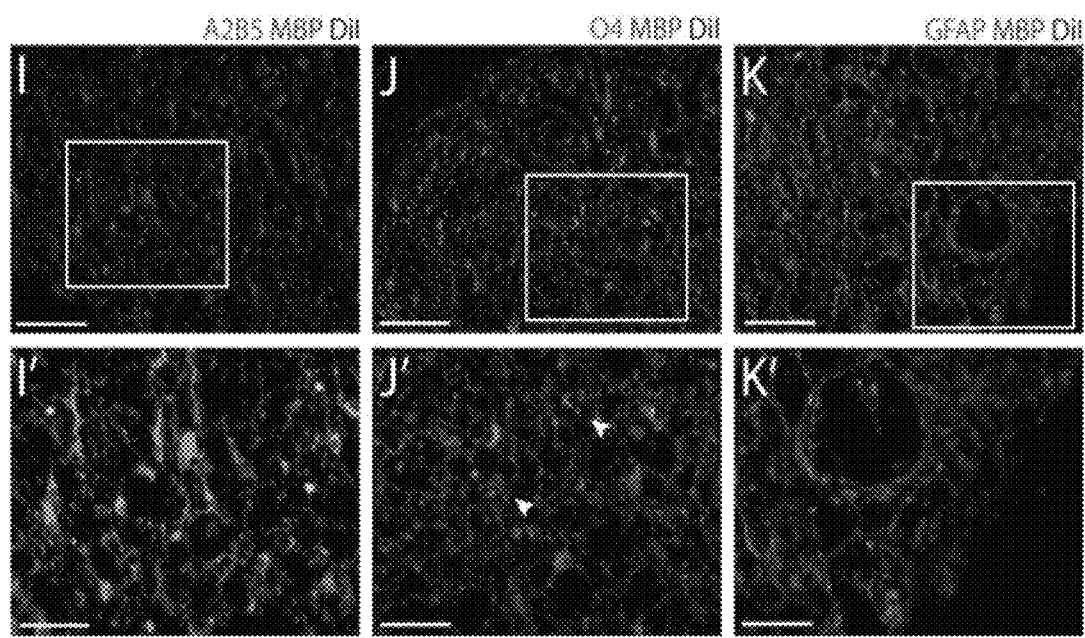
FIG. 4c illustrates the results of differentiation of iOPCs transplanted into the spinal cord of a rat into O4, MBP and GFAP positive cells, and A2B5 immature marker expression of undifferentiated iOPCs (I and I'), in which the white arrows in r indicate O4 positive and MBP positive cells, and scale bars are 100 μm and 50 μm.

In order to evaluate functional characteristics of iOPCs in vivo, cells were transplanted into spinal cord injured adult rats. To this end, iOPCs were injected into the injured spinal cord until one week after spinal cord injury, and the results were observed until 12 weeks. To observe the restoration of the injured portion, the spinal cord was stained by H&E. The extent of the tissue injury in the injured portion was decreased further in the iOPC-injected group than in the control (FIG. 4a) Immunohistochemical staining was performed, whereby engraftment of the transplanted cells was confirmed. In the transplanted bone marrow, O4, MBP and GFAP positive cells were observed in large amounts, but were seldom observed in the fibroblast-transplanted rat (C to H of FIG. 4b). In the restored spinal cord cells, the injured portion was stained with the oligodendrocyte markers A2B5, O4, MBP and GFAP (I to K of FIG. 4c). The A2B5 and O4 positive cells expressed MBP in common, but the GFAP positive cells did not express MBP. Thereby, the transplanted iOPCs were proven to differentiate into either myelination oligodendrocytes or GFAP positive astrocytes. To exclude the concern of tumor genes, iOPCs were injected into a mouse, and whether tumors were formed was checked until 8 months after injection. Consequently, the transplanted iOPCs were proven to restore the myelination in the spinal cord without the generation of tumors, and to restore the injured portion of the spinal cord injured rat.

6. Gene Expression of iOPCs manufactured using only Single Gene among Direct Transdifferentiation Factors SOX1, SOX2, SOX10, OLIG2, NKX2.2, and NKX6.2

Figure 6:
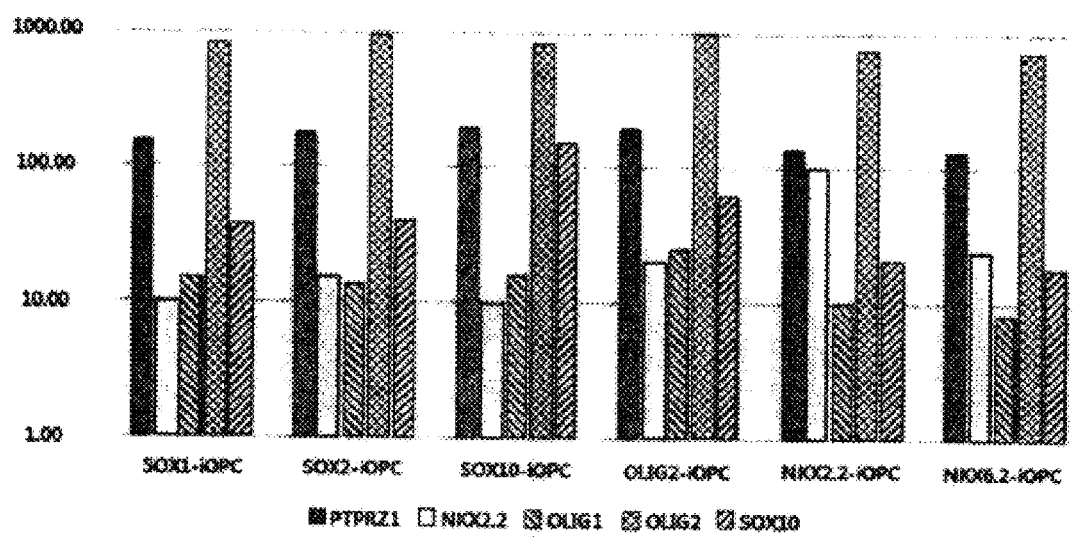
FIG. 6 illustrates the results of quantitative RT-PCR of iOPCs induced by SOX1, SOX2, SOX10, OLIG2, NKX2.2, or NKX6.2 for gene expression of OPC-based markers and oligodendrocyte markers, in which the graph is shown in log 2 fold change normalized to GAPDH.

Using only a single gene, among SOX1, SOX2, SOX10, OLIG2, NKX2.2, and NKX6.2 genes, important for the development of the nervous system, iOPCs were induced. Based on the results of mRNA expression of OPC-specific genes of iOPCs manufactured from individual genes, PTPRZ1, NKX2.2, OLIG2, OLIG1 and SOX10 manifested high expression (FIG. 6).

The invention claimed is:

1. A method of inducing a direct transdifferentiation of a somatic cell into an oligodendrocyte progenitor cell, comprising
    introducing to a somatic cell a protein which is OCT4, or a combination of OCT4 and at least one selected from the group consisting of SOX1, SOX2, SOX10, OLIG2, NKX2.2, and NKX6.2,
    a nucleic acid molecule encoding the protein, or
    a vector comprising the nucleic acid molecule; and
    culturing the somatic cell in a medium comprising PDGF-AA,
    wherein the somatic cell is a cell selected from the group consisting of a fibroblast, a nerve cell, an astrocyte, a neural stem cell, a cord blood stem cell, and a mesenchymal stem cell.

2. The method of claim 1, wherein the protein is OCT4.

3. The method of claim 1, wherein the vector is at least one selected from the group consisting of a plasmid vector, a cosmid vector, a viral vector, and an episomal vector.

4. The method of claim 3, wherein the viral vector is at least one selected from the group consisting of a retrovirus vector, an adenovirus vector, an adeno-associated virus vector, and a Herpes simplex virus vector.

5. The method of claim 4, wherein the retrovirus vector is at least one selected from the group consisting of a HIV (Human Immunodeficiency Virus) vector, a MLV (Murine Leukemia Virus) vector, an ASLV (Avian Sarcoma/Leukosis) vector, a SNV (Spleen Necrosis Virus) vector, a RSV (Rous Sarcoma Virus) vector, and a MMTV (Mouse Mammary Tumor Virus) vector.

* * * * *